United States Patent
Shiozawa

(10) Patent No.: US 6,320,700 B2
(45) Date of Patent: Nov. 20, 2001

(54) LIGHT-TRANSMITTING OPTICAL MEMBER, MANUFACTURING METHOD THEREOF, EVALUATION METHOD THEREFOR, AND OPTICAL LITHOGRAPHY APPARATUS USING THE OPTICAL MEMBER

(75) Inventor: Masaki Shiozawa, Sagamihara (JP)

(73) Assignee: Nikon Corporation, Tokyo (JP)

( * ) Notice: Subject to any disclaimer, the term of this patent is extended or adjusted under 35 U.S.C. 154(b) by 0 days.

(21) Appl. No.: 09/791,892

(22) Filed: Feb. 26, 2001

Related U.S. Application Data

(62) Division of application No. 09/389,462, filed on Sep. 3, 1999, now Pat. No. 6,226,128.

(30) Foreign Application Priority Data

Sep. 8, 1998 (JP) .................................................. 10-252554

(51) Int. Cl.$^7$ .............................. G02B 11/00; G02B 3/00; G02B 27/02
(52) U.S. Cl. ......................... 359/642; 359/722; 359/800; 359/350
(58) Field of Search .................................. 359/642, 722, 359/800, 350

(56) References Cited

U.S. PATENT DOCUMENTS

| | | | |
|---|---|---|---|
| 4,358,543 | 11/1982 | Nozawa | 501/40 |
| 4,757,354 | 7/1988 | Sato et al. | 355/53 |
| 5,045,507 | 9/1991 | Tran | 501/40 |
| 5,696,624 | 12/1997 | Komine et al. | 359/350 |
| 6,226,128 * | 5/2001 | Shiozawa | 359/642 |

FOREIGN PATENT DOCUMENTS

| | | |
|---|---|---|
| 0908716 A1 | 4/1999 | (EP) . |
| 10001310 A | 1/1998 | (JP) . |

* cited by examiner

Primary Examiner—Georgia Epps
Assistant Examiner—Michael A. Lucas
(74) Attorney, Agent, or Firm—Morgan, Lewis & Bockius LLP

(57) ABSTRACT

An optical member for transmitting light of a wavelength less than about 200 nm including crystalline calcium fluoride with a potassium content less than about 0.5 ppm, wherein a degradation in a transmissivity of the optical member after an irradiation for a fixed period of time with the light of the wavelength of less than about 200 nm is less than about 5% of a transmissivity of the optical member before the irradiation.

1 Claim, 4 Drawing Sheets

TRANSMISSIVITY PERMANENCE
VERSUS POTASSIUM CONTENT

LIGHT-TRANSMITTING OPTICAL MEMBER, MANUFACTURING METHOD THEREOF, EVALUATION METHOD THEREFOR, AND OPTICAL LITHOGRAPHY APPARATUS USING THE OPTICAL MEMBER

This is a divisional of application(s) application Ser. No. 09/389,462 filed on Sep. 3, 1999 now U.S. Pat. No. 6,226,128.

This application claims the benefit of Japanese Application No. 10-252554, filed in Japan on Sep. 7, 1998, which is hereby incorporated by reference.

BACKGROUND OF THE INVENTION

1. Field of the Invention

The present invention relates to a light-transmitting optical member, and more particularly, to a light-transmitting optical component (such as a lens, prism, plate, etc.) that is used in an optical system (such as a lithography apparatus, CVD device, laser processing device, etc.) with a light source (such as an ArF excimer laser, $F_2$ laser, solid state laser, etc.) having a wavelength below 200 nm. The present invention also relates to a manufacturing method and an evaluation method for such a light-transmitting optical component.

2. Discussion of the Related Art

An optical lithography process uses a lens (light-transmitting optical member or component) to direct light from an exposure light source through a mask to a wafer coated with a photo-sensitive material, thereby transferring a pattern on the mask onto the wafer. LSIs are being developed with increasingly high density. Generally, the resolving power of the transferred pattern is inversely proportional to the numerical aperture of the lens and directly proportional to the exposure light wavelength. The numerical aperture of the lens increases as the diameter of the lens increases. However, it is difficult to increase the numerical aperture of the lens past a certain limit, because an impractically large diameter is required. For this reason, a reduction in the wavelength of the light source is desired in order to allow a further improvement in resolution in an optical lithography process.

Until now, light sources used in optical lithography have utilized ultraviolet light including the i-line (365 nm) of a high pressure mercury lamp and a shorter wavelength light (248 nm) of a KrF excimer laser. Because the KrF excimer laser is capable of high power output with a high laser oscillation frequency, the KrF excimer laser has been widely used as an efficient light source for optical lithography, and research and development continues to increase its efficiency. As a result of this wide use of ultraviolet light, optical lenses with high ultraviolet transmissivity have been increasingly used in the optical systems of optical lithography apparatus.

Recently, to improve the resolution further, it is expected that light sources producing vacuum ultraviolet light of even shorter wavelengths will be used in optical lithography apparatus.

Although high-light-transmittance optical lenses are used in conventional optical lithography apparatus, these conventional lenses cannot provide the practical degree of transparency needed with vacuum ultraviolet light of a shorter wavelength (about 200 nm or less). This problem has prevented the use of vacuum ultraviolet light sources in optical lithography processes. Vacuum ultraviolet light has a high energy, more than about 6.2 eV. Therefore, if the transmittance of a lens is not sufficiently high, the energy which is not transmitted by the lens is converted to heat, and as a result, the imaging performance deteriorates due to thermal expansion of the optical lens. Also, with such an insufficient transmittance, a photo-resist cannot be properly exposed.

SUMMARY OF THE INVENTION

Accordingly, the present invention is directed to a manufacturing method, evaluation method, and optical lithography apparatus for a light-transmitting optical component that substantially obviates the problems due to limitations and disadvantages of the related art.

An object of the present invention is to provide an optical lens having superior optical properties required by an optical lithography apparatus using a vacuum ultraviolet light source with a wavelength below 200 nm.

Another object of the present invention is to provide a method for evaluating of a light-transmitting optical component that transmits light with a wavelength below 200 nm to determine whether the optical component can be used in an optical lithography apparatus using vacuum ultraviolet light source.

Additional features and advantages of the invention will be set forth in the description which follows, and in part will be apparent from the description, or may be learned by practice of the invention. The objectives and other advantages of the invention will be realized and attained by the structure particularly pointed out in the written description and claims hereof as well as the appended drawings.

To achieve these and other advantages and in accordance with the purpose of the present invention, as embodied and broadly described, the present invention provides a light-transmitting optical member for transmitting light with a wavelength less than about 200 nm, the optical member including crystalline calcium fluoride with a potassium content less than about 0.5 ppm, and the optical member having a degradation in a transmittance of less than 5% after irradiation for a predetermined period of time with light of a wavelength less than about 200 nm.

In another aspect, the present invention provides a method for evaluating a light-transmitting optical member for use with light of a wavelength less than about 200 nm, the method including the steps of measuring a first transmissivity of the optical component, thereafter irradiating the optical component with light of a wavelength less than about 200 nm for a predetermined time period, measuring a second transmissivity of the optical component that was irradiated in the step of irradiating to determine an amount of a transmissivity decrease after the irradiation, and comparing the amount of transmissivity decrease with a predetermined value to determine whether the light transmitting component is usable in an optical lithography apparatus.

In another aspect, the present invention provides a method for manufacturing a light-transmitting optical member that transmits light of a wavelength less than about 200 nm, the method including the steps of melting a calcium fluoride raw material, and gradually cooling the melted raw material with a temperature gradient at a solid-melt interface to crystallize calcium fluoride, wherein a potassium content in the raw material and the temperature gradient are adapted to provide for the potassium content of the resulting crystal to be less than about 0.5 ppm in a pulling-down scheme.

In another aspect, the present invention provides a method for the manufacture of a light-transmitting optical member that transmits light of a wavelength less than about 200 nm, the method including the steps of melting within a crystal growth crucible of calcium fluoride raw material with a potassium content less than 0.5 ppm, a crystal growth step during which gradual cooling and crystal growth are carried out, and a heat treatment step during which, after maintenance of the obtained grown calcium fluoride crystal at a high temperature, the calcium fluoride crystal is gradually cooled.

In another aspect, the present invention provides an optical lithography apparatus including an illumination optical system that emits exposure light of a wavelength less than about 200 nm towards a mask having a pattern, and a projection optical system that projects an image of the pattern on the mask onto a substrate, wherein at least one of the illumination optical system and the projection optical system includes a light-transmitting optical member formed of crystalline calcium fluoride with a potassium content less than about 0.5 ppm.

It is to be understood that both the foregoing general description and the following detailed description are exemplary and explanatory, and are intended to provide further explanation of the invention as claimed.

BRIEF DESCRIPTION OF THE DRAWINGS

The accompanying drawings, which are included to provide a further understanding of the invention and are incorporated in and constitute a part of the specification, illustrate embodiments of the invention and together with the description serve to explain the principles of the invention.

In the drawings.

DETAILED DESCRIPTION OF THE PREFERRED EMBODIMENTS

Figure 1:
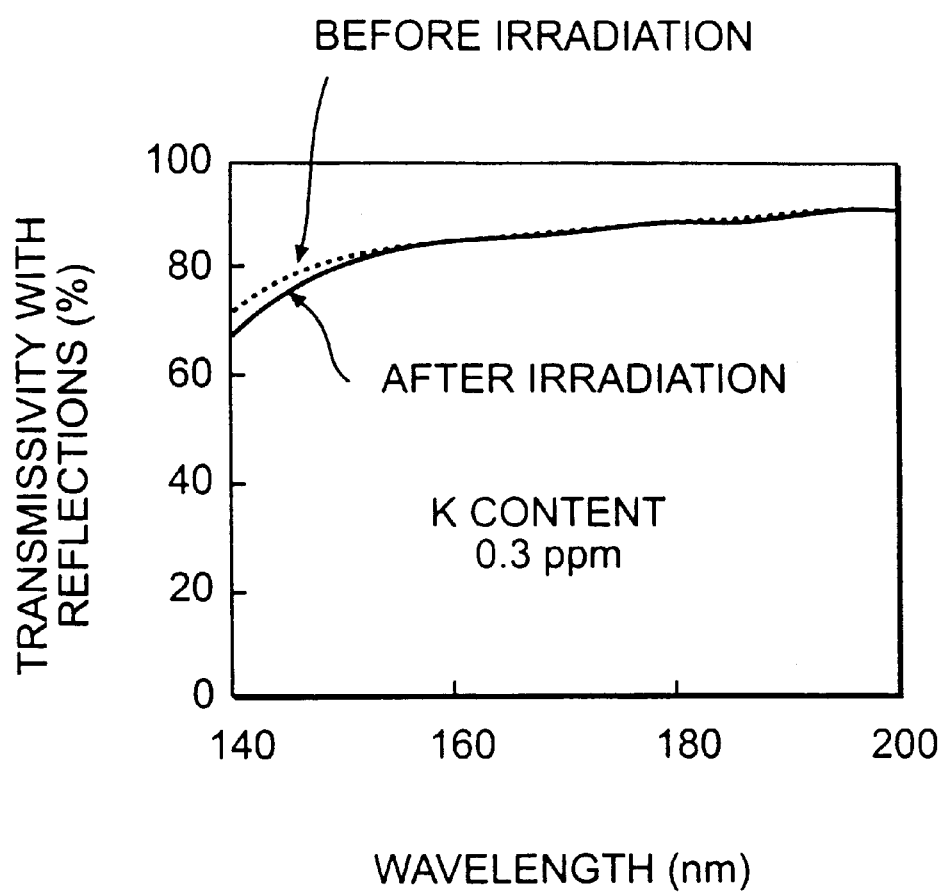
FIG. 1 is a graph showing measured transmissivity versus wavelength for the reduced-potassium-content crystalline calcium fluoride of Working Example 1 of the invention.

Reference will now be made in detail to the preferred embodiments of the present invention, examples of which are illustrated in the accompanying drawings.

Before describing the preferred embodiments of the present invention, results of the inventor's diligent research and development, which lead to the present invention, are described.

To overcome the problems of the conventional art, it may be seen that fluoride type compound crystals may be used as optical materials because they possess a smaller short-wavelength absorption edge (shorter cutoff wavelength). Examples of these compound crystals include, but are not limited to, crystalline lithium fluoride (LiF), crystalline magnesium fluoride ($MgF_2$), crystalline calcium fluoride ($CaF_2$), etc. The use of crystalline lithium fluoride is impractical for an optical lens due to its extremely high hygroscopicity. Crystalline magnesium fluoride is known to exhibit birefringence phenomena as a result of optical anisotropy, and is therefore also impractical for use as an optical lens.

The cutoff wavelength of crystalline calcium fluoride is 124 nm. Crystalline calcium fluoride lacks such severe hygroscopicity, lacks optical anisotropy, and is transparent to vacuum ultraviolet wavelengths. For these reasons, crystalline calcium fluoride may be used as an optical material for an optical lithography apparatus when a vacuum ultraviolet light source is desired.

The present inventor conducted a diligent research for developing a method for determining whether a sufficient level of transparency in the vacuum ultraviolet wavelengths could be maintained, thus allowing the material to be used in an optical lithography apparatus. The material must exhibit a sufficient durability with respect to its transmissivity (transmissivity permanence): i.e. it needs to have acceptable transmissivity by the optical material prior to irradiation by (illumination using) vacuum ultraviolet light and acceptable transmissivity by the optical material after degradation due to irradiation by (illumination using) vacuum ultraviolet light. It was discovered that a material with a small transmissivity loss (difference between the post-illumination transmissivity and the pre-illumination transmissivity) can be used as an optical component for optical lithography.

Accordingly, the present invention provides a method of evaluating the light-transmitting optical member, the method including the steps of measuring a transmissivity of the optical component, thereafter irradiating the optical component with light of a wavelength less than about 200 nm for a predetermined time period, measuring a transmissivity of the optical component that was irradiated in the step of irradiating to determine an amount of a transmissivity decrease after the irradiation, and comparing the amount of transmissivity decrease with a predetermined value to determine whether the light transmitting component is usable in an optical lithography apparatus.

The inventor also experimentally discovered factors that mainly contribute to degradation of transmittance for the vacuum ultraviolet light of wavelengths below 200 nm. It was hypothesized that the existence of point defects, due to impurities contained within the calcium fluoride crystal, might be a cause for the transmissivity loss. This hypothesis was tested by conducting crystal growth experiments in which certain impurities were added during the crystal manufacturing process. These experiments revealed that a potassium composition, among impurities contained within crystalline calcium fluoride, caused a degradation of transmissivity after irradiation by a vacuum ultraviolet light.

Accordingly, the present invention provides, in another aspect, a light-transmitting-optical component that transmits light of a wavelength less than about 200 nm, wherein the optical component is mainly composed of crystalline calcium fluoride with a potassium content of less than about 0.5 ppm, and after irradiation for a fixed time period using light of a wavelength less than about 200 nm, the difference in transmissivity before and after irradiation is less than 5%.

The present inventor discovered a method of manufacturing such a high quality optical member, the method including the steps of melting a calcium fluoride raw material having a potassium content, and gradually cooling the raw material at a temperature gradient in a pulling-down scheme to crystallize calcium fluoride, wherein at least one of the following is carried out: (1) the use of calcium fluoride raw material with a low potassium content, (2) pre-heating of the raw material at a high temperature, and (3) reduction of potassium during crystal growth.

It was determined that an optical component with excellent transmissivity permanence could be manufactured by use of the above three steps. Among the three steps, the use of any single step is effective. Preferably, the combined use of any two or all three of these steps provides for a further improved transmissivity permanence.

A method of evaluating the transmissivity permanence (durability in transmissivity against radiation) of an optical component according to the present invention will be explained next.

Transmissivity permanence is evaluated by testing (a permanence test) an optical material using light from a light source that is suitable for use in a vacuum ultraviolet light lithography apparatus. This testing compares the measurements of transmissivity of an optical material prior to irradiation and after irradiation by a light source with an energy density that is the same as, or greater than, that suitable for use in a vacuum ultraviolet light lithography apparatus.

Examples of these light sources include, but are not limited to, ArF laser (193 nm), $Xe_2$ lamp (172 nm), $F_2$ laser (157 nm), $Kr_2$ lamp (146 nm), and solid state lasers. An evaluation (a permanence test) light source can be selected to have the same wavelength as that of a light source for actual lithography apparatus. Alternatively, evaluation can also be carried out using the comparatively shorter wavelength of the $Kr_2$ lamp. Neither the evaluation light source nor the light source for the optical lithography apparatus is limited to these particular light sources.

When crystalline calcium fluoride is irradiated at a fixed energy density by a vacuum ultraviolet light with a wavelength below 200 nm, the transmissivity gradually decreases and approaches a substantially constant minimum value. According to the evaluation method of the present invention, irradiation continues for a fixed time period until the transmissivity substantially reaches a constant minimum value. A time period of one hour is generally a sufficient fixed time period, as the required time period tends to be of this length or less for irradiation at high energy density.

This post-irradiation sample is then prepared for transmissivity measurement. The post-irradiation sample is preferably mechanically processed to a thickness of 0.3 to 5 cm, regardless of the degree of crystallinity (whether single crystal or polycrystalline) of the crystalline calcium fluoride. Then two parallel surfaces of the sample preferably are polished. The sample then preferably undergoes wet-type cleaning so as to ensure a superior surface cleanliness needed for precise measurement of transmissivity. The sample thickness should be such that the sample can be placed in a measurement equipment for measuring transmissivity. The sample thickness is preferably at least about 0.3 cm in order to avoid any difficulties during post-irradiation measurement of transmissivity that may be caused by excessive thinness.

During the evaluation method of the present invention, the spectroscopic transmissivity of the sample is first measured prior to irradiation by vacuum ultraviolet light. The measured transmissivity is referred to as the "first transmissivity".

This sample is then irradiated at a desired energy density using vacuum ultraviolet light. After the transmittance has decreased to a substantially constant minimum value, the spectroscopic transmissivity is measured for the irradiated portion (the same portion of the sample that transmitted the irradiating light). This transmissivity is referred to as the "second transmissivity".

The transmissivity permanence is then evaluated. The transmissivity permanence is determined based on a comparison of the pre-irradiation and post-irradiation transmissivities (first and second transmissivities). The transmissivity permanence is determined to be unacceptable if the transmissivity decline is found to be larger than a predetermined limit. The degradation of transmissivity is quantitatively expressed in terms of the pre-versus-post-irradiation transmissivity difference.

When the transmissivity permanence of multiple samples was evaluated by the above method, it was discovered that for many samples, the post-irradiation transmissivity declines despite excellent transmissivity prior to irradiation. In many cases calcium fluoride crystals which possessed a high transmissivity prior to irradiation by vacuum ultraviolet light degraded below an acceptable limit of transmissivity after exposure to vacuum ultraviolet light. This phenomenon was understood to show that the prior art method of crystalline calcium fluoride transmissivity measurement only prior to irradiation is insufficient for determining the transmissivity permanence of an optical lens for a vacuum ultraviolet lithography apparatus. Thus, the present inventor discovered, contrary to the conventional view that transmissivity after vacuum ultraviolet irradiation would be acceptable if the pre-irradiation transmissivity was acceptable, the two transmissivities were not necessarily so related.

Accordingly, the optical component of the present invention is characterized by a transmissivity decrease of less than about 5%. The present inventor has found that if the transmissivity decrease is less than about 5%, the optical component of the present invention can be utilized in a vacuum ultraviolet optical lithography apparatus, because the transmissivity permanence of the optical component is acceptable.

The present inventor further investigated factors that maintain transmissivity permanence in vacuum ultraviolet wavelengths below about 200 nm. As stated above, it was hypothesized that the existence of point defects, due to impurities contained within the calcium fluoride crystal, might be a cause for transmissivity loss. This hypothesis was tested by conducting crystal growth experiments in which certain impurities were added during the crystal manufacturing process. These tests revealed that a potassium composition, among the impurities contained within crystalline calcium fluoride, causes the degradation of transmissivity after irradiation by vacuum ultraviolet light.

Figure 2:
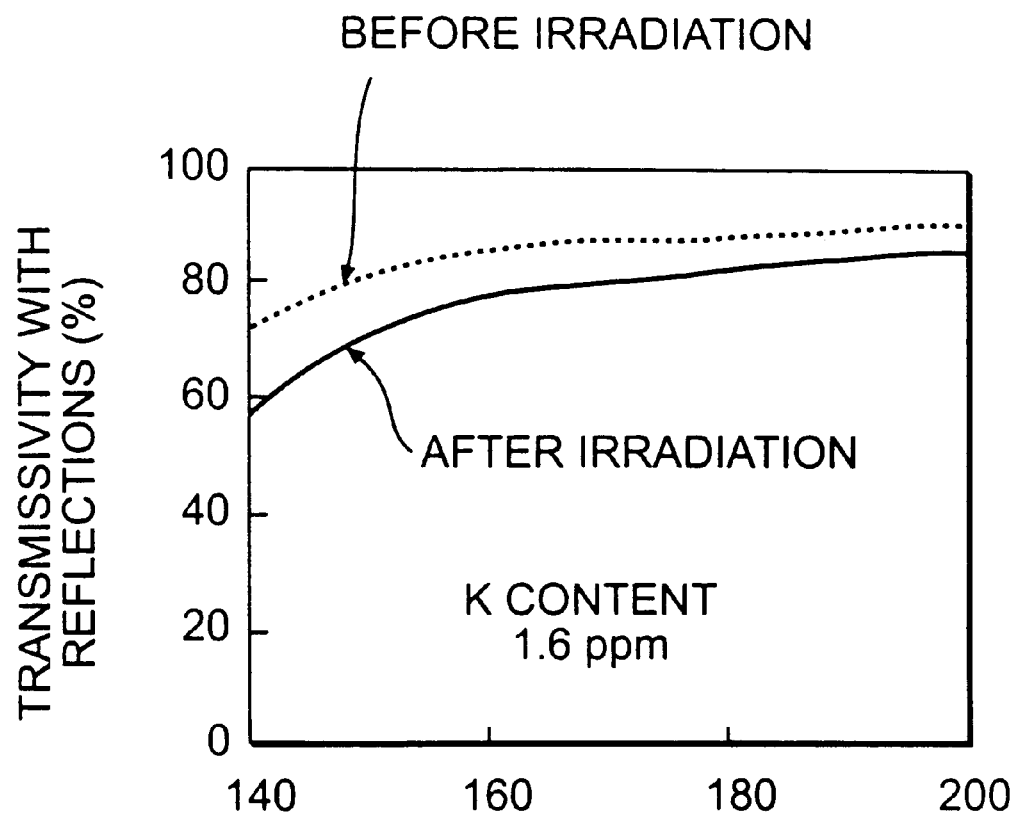
FIG. 2 is a graph showing measured transmissivity versus wavelength by the crystalline calcium fluoride of Comparative Example 1.

FIG. 1 shows a graph of the pre-irradiation and post-irradiation transmissivity curves (including reflections) for crystalline calcium fluoride having a 0.3 ppm potassium content. FIG. 2 shows a graph of the pre-irradiation and post-irradiation transmissivity curves (including reflections) for crystalline calcium fluoride has a 1.6 ppm potassium content. These results show that transmissivity permanences of calcium fluoride crystals differ with crystal potassium content, even when the pre-irradiation transmissivities are high and equal.

Samples were next prepared from calcium fluoride crystals manufactured with different potassium contents, and transmissivity permanence tests were carried out. The results indicated that lowering the potassium content within crystalline calcium fluoride is effective in improving the transmissivity permanence of crystalline calcium fluoride at vacuum ultraviolet wavelengths.

It was also discovered that the potassium content can be effectively reduced by the following steps: (1) the use of calcium fluoride raw material with a low potassium content, (2) maintaining the raw material at a high temperature (annealing), and (3) reducing potassium during crystal growth. It is preferable to use all the steps 1–3 to significantly reduce potassium content. However, if desired, only one or two of the steps may be employed depending on specific needs.

The use of calcium fluoride raw material with a low potassium content will be explained. It is desirable to begin with a high purity raw material in order to improve the optical characterisics of the post-grown crystal. Selection of a raw material with an improved overall calcium fluoride purity (99.9%, 99.99%, etc. as an improvement over 99% pure) is insufficient. In order to obtain crystalline calcium fluoride with superior transmissivity permanence to vacuum ultraviolet light, a raw material that is purified with respect to the potassium content is desired. Thus, a calcium fluoride raw material of the present invention has a potassium content preferably below about 0.5 ppm. This quantitative determination of the preferable potassium concentration within the raw material was conducted using the atomic absorption spectrochemical analysis.

A method for maintaining the raw material at high temperature (annealing) will be explained. The heat treatment step preferably includes heating the calcium fluoride raw material under vacuum and maintaining the calcium fluoride raw material at a temperature as high as possible below the melting point. The heat treatment temperature can be set at an arbitrary temperature within the 800 to 1300° C. range, for example. Calcium fluoride in the powder form may be treated at the relatively low temperature of 1000° C. A powder type cullet or large chunks should preferably be treated at a temperature as high as possible, such as 1300° C., near but below the melting point. A heat treatment temperature of at least 800° C. is desirable in order to sufficiently remove potassium. The annealing temperature of less than the melting point is preferable because at that temperature potassium does not remain in the material as it would do so if the annealing temperature were above the melting point.

A maintenance time period of one hour for the high temperature heat treatment is effective. Of course, a heat treatment for a longer time period is also effective. A powder type cullet or large chunks should preferably be treated for a comparatively long time period, such as 10 or more hours. The potassium content of the calcium fluoride raw material is removed by this treatment.

Next, a method for reducing the potassium concentration during crystal growth will be explained. A suitable method for crystal growth is solidification from a melt. A temperature gradient of at least about 8° C./cm is desired in the vicinity of the solid-melt interface during crystal growth. The uptake of potassium by the calcium fluoride crystal from the calcium fluoride melt during solidification (crystallization) was found to become extremely low by establishment of such a high temperature gradient. Conversely, it is found that, when the temperature gradient is less than about 8° C./cm, potassium within the melt is easily taken up by the calcium fluoride crystal. Although a temperature gradient well above 8° C./cm is desirable, a higher gradient may be difficult to achieve due to a number of factors, including increased complexity of equipment, higher equipment cost, etc. In consideration of such difficulties, a preferred range for the temperature gradient is about 8 to about 20° C./cm.

Although the potassium content can be reduced by use of the temperature gradient during crystal growth, additional reduction of the potassium content through selection of a raw material with a lower potassium content, as described above, is more preferred.

One may select an optical component for a vacuum ultraviolet lithography apparatus by measuring the potassium content. Specifically, when crystalline calcium fluoride is used for an optical lens of a lithography apparatus, the potassium content and the vacuum ultraviolet intensity (density) should be considered. Vacuum ultraviolet light intensity is related to the numerical aperture of the optical lens. Vacuum ultraviolet light is concentrated in a small region when the numerical aperture of the optical lens is small. A lower potassium concentration is needed when the numerical aperture of the optical lens is small. When the numerical aperture of the optical lens is large, vacuum ultraviolet light is not concentrated within a small region. Thus, the potassium content is not necessarily as low as that required for the small diameter when the numerical aperture of the optical lens is large.

Figure 4:
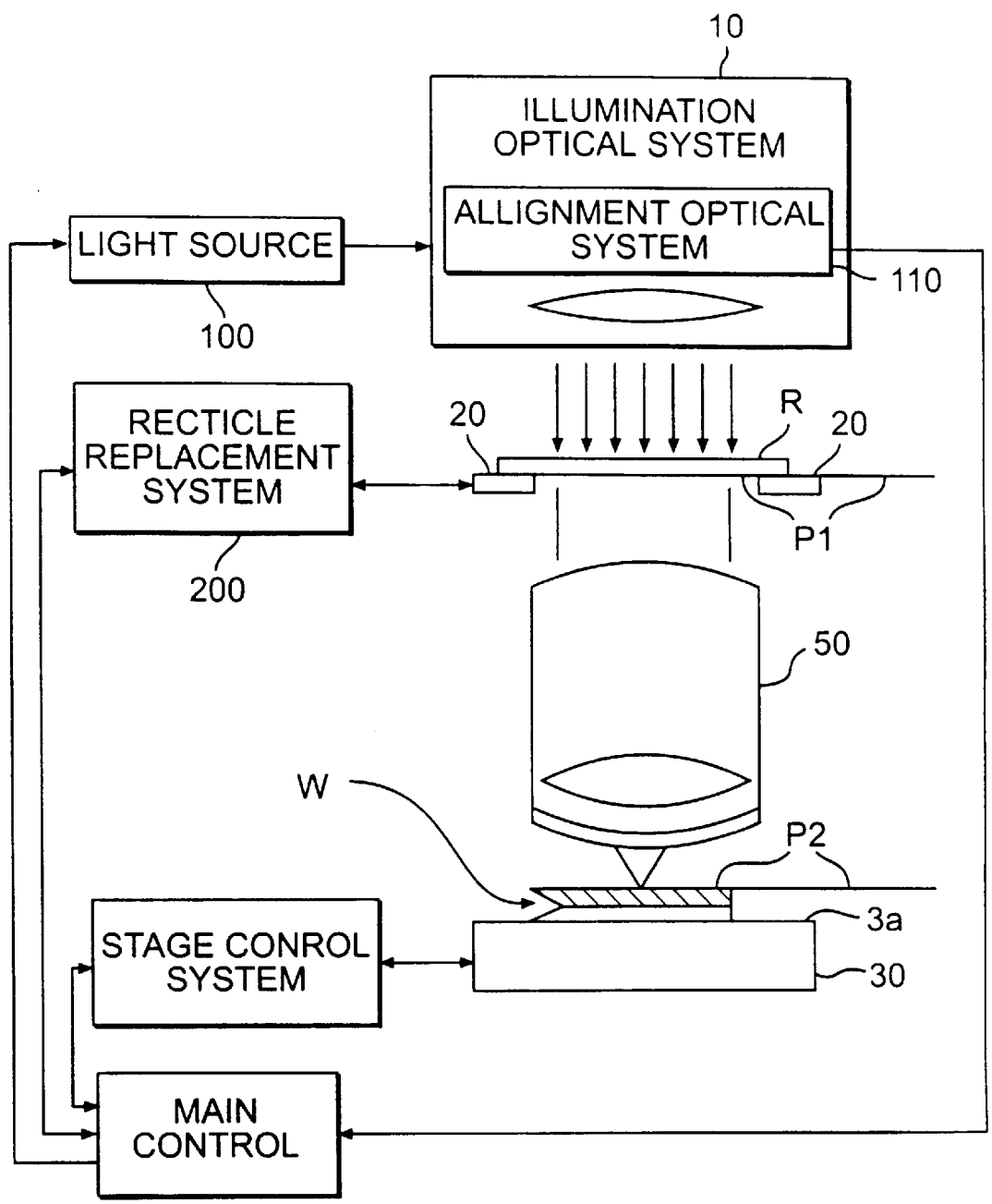
FIG. 4 schematically illustrates an optical lithography apparatus of the present invention.

FIG. 4 shows the basic construction of an example of an optical lithography apparatus according to the present invention. In FIG. 4, item 30 is a stage having a surface 3a upon which a substrate (wafer) W is placed. A surface of substrate W is coated with a photo-sensitive material. An illumination optical system 10 is provided to uniformly illuminate a mask (reticle) R with a light (exposure light) having a wavelength below about 200 nm, such as ArF excimer laser light. An integrated circuit pattern is drawn on the mask R. A light source 100 supplies exposure light to the illumination optical system 10. In order to project a reduced image of the pattern of the mask R onto the substrate W, a projection optical system 50 is placed between a first plane P1 (object plane) of the mask R and a second plane P2 (image plane that is located to coincide with the surface of the substrate W). The illumination optical system 10 also includes an alignment optical system 110 to adjust the position of the mask R relative to the substrate W. The mask R is placed on a reticle stage 20 so that the mask R is movable parallel to the surface of a wafer stage 30. A reticle replacement system 200 is provided for transferring and replacing the reticle R set in the reticle stage 20. The reticle replacement system 200 includes a stage driver for moving the reticle stage 20 parallel to the surface 3a of the wafer stage 30, for example. The projection optical system 50 has an alignment optical system for use by a scanning type apparatus, for example.

In addition to the scanning type apparatus (that exposes the mask pattern while synchronously moving the mask and substrate), the optical lithography apparatus of the present invention may be a step-and-repeat type exposure apparatus that exposes the mask pattern while the mask and substrate are at rest, and then moves the wafer to another position (the step) to expose a different area of the wafer with the same mask pattern.

The light source utilized by the optical lithography apparatus of the present invention is in the vacuum ultraviolet region below about 200 nm. The examples include, but are not limited to, an ArF (193 nm) laser, $F_2$ (157 nm) laser, etc.

The optical lithography apparatus of the present invention utilizes an optical component in at least one of the above mentioned illumination optical system 10 and projection optical system 50, wherein the optical component is constructed from crystalline calcium fluoride that has a potassium content less than about 0.5 ppm, and a difference of less than about 5% in transmissivity before and after irradiation for a fixed time period using light of a certain wavelength less than about 200 nm. Use of such an optical element is particularly effective in the illumination optical system. This is because the illumination optical system is closer to the light source and each lens component in the illumination optical system is illuminated at a high energy density by light spanning a comparatively narrow light path. For these reasons, an optical element located in the illumination optical system requires a rather high transmissivity permanence.

Energy density increases as vacuum ultraviolet light is concentrated into a stronger illumination by a small aperture lens. Because crystalline calcium fluoride with a potassium content below about 0.1 ppm was discovered to have an excellent transmissivity permanence, such crystalline calcium fluoride is particularly preferable for use in a lens having an aperture below about 100 mm. Of course, such high quality crystalline calcium fluoride is not limited to this aperture size, and may be used for an optical lens of any aperture size to provide for superior characteristics.

Crystalline calcium fluoride with a potassium content of up to about 0.5 ppm is used for lenses of apertures greater than about 100 mm, more preferably for lenses with apertures greater than about 200 mm. Because such crystalline calcium fluoride with a potassium content of up to about 0.5 ppm still has an excellent transmissivity permanence, it may be used for optical lenses of any aperture depending on particular needs.

Crystalline calcium fluoride with a potassium content above about 0.5 ppm has poor transmissivity permanence of vacuum ultraviolet light. Crystalline calcium fluoride of this composition may not be suitable for use in an optical lens of an optical lithography apparatus which processes vacuum ultraviolet light.

The optical lithography apparatus of the present invention uses the above mentioned crystalline calcium fluoride optical component having an excellent transmissivity permanence. Accordingly, the optical lithography apparatus of the present invention can process shorter wavelength light than that of conventional optical lithography apparatus.

Various samples of calcium fluoride were manufactured to provide for working examples of the present invention and comparative examples, as follows.

WORKING EXAMPLE 1

Calcium fluoride powder with a potassium content of 0.5 ppm was used as raw material for manufacturing Working Example 1 of crystalline calcium fluoride of the present invention. Quantitative determination of the potassium concentration within the powder raw material was carried out by the atomic absorption spectrochemical analysis.

The powder raw material then underwent a high temperature heat treatment. The following are necessary to carry out the high temperature heat treatment. First, a vacuum pump is required to apply vacuum. A final pressure below 0.001 atm is required during the high temperature heat treatment. An oil diffusion pump was used to attain this low pressure. Second, a container is needed to hold the calcium fluoride powder. Of course, the material of this container should be potassium-free, should withstand temperature conditions of as much as 1300° C., should undergo no chemical reaction with calcium fluoride, and should not adhere to high temperature calcium fluoride. A container constructed from graphite was used for manufacturing the example of the present invention. A heating unit is also needed. A graphite heater element was placed at the perimeter of the container, and high temperature of the calcium fluoride was maintained by electrical current heating. During this high temperature heat treatment, the container temperature was measured using a thermocouple. According to a preplanned temperature profile, temperature was raised, maintained at a high value, and lowered, as follows. The container held 10 kg of the powder raw material. The container was placed at a prescribed position within the high temperature heat treatment apparatus, and then vacuumed. After vacuumed for over 1 hour, a pressure below 0.001 atm was achieved. Then the container was heated to 1000° C. during a 1 hour time period. After maintaining the container for 3 hours at the high temperature, the temperature was dropped to room temperature during a 10 minute time period. A 5 hour time period was required for the powder raw material to cool down to near room temperature. Vacuum was cut off, and the powder raw material was taken out.

The vertical Bridgeman method was used for crystal growth. Two heater elements (with independent power circuits, independent settings, and independent control) were provided above and below the solid-melt interface to control the temperature gradient at the interface. The temperatures of the heater elements were measured by radiation thermometers (pyrometers). The distance between the measurement locations of these pyrometers was set to 10 cm. For example, the temperature gradient would be determined to be 10° C./cm if the temperature difference of the top and bottom heater elements was 100° C. A crucible was charged with the powder raw material that had undergone the high temperature heat treatment above, and a chamber was vacuumed. The temperature was raised under precise temperature control, and the raw material was melted. The temperature gradient was set to 10° C./cm since a wide temperature difference between the upper and lower heater elements was desirable. Then crystallization was carried out by a pulling-down scheme at a rate of 1 mm per hour from the high temperature zone to the low temperature zone.

A permanence test sample was prepared from the crystalline calcium fluoride obtained in this manner. This sample was 5.08 cm (2 inches) in diameter and 2.54 cm (1 inch) in thickness. Accuracy of thickness processing was ±0.01 cm. The two parallel surfaces were parallel within 30 sec. The RMS surface roughness of the mirror-polished surfaces was less than 5 Å. The mirror polished sample surfaces underwent surface cleaning treatment: ultrasonic cleaning using organic solvent, followed by rinsing with purified water, and then drying using isopropyl alcohol vapor.

The transmissivity of this sample at 140 to 200 nm was measured by spectroscopy (spectroscopic transmissivity). Permanence testing was carried out using a light source producing vacuum ultraviolet light with a 146 nm central wavelength. The irradiation device was a head-on type barrier discharge lamp manufactured by Ushio Denki K.K. The intensity of the vacuum ultraviolet radiation from this lamp was 15 mW/cm$^2$. The entire vacuum ultraviolet light path was purged with nitrogen during the permanence testing to prevent absorption by oxygen. After irradiation of the sample by the vacuum ultraviolet light for 1 hour, the spectroscopic transmissivity at 140 to 200 nm was measured again. FIG. 1 shows the transmissivity curves (including reflections) before and after radiation with the vacuum ultraviolet light. As shown in FIG. 1, almost no decline in transmissivity occurred upon irradiation by vacuum ultraviolet light. The potassium content of the sample was measured by the atomic absorption spectrochemical analysis and found to be 0.3 ppm.

Comparative Example 1

Calcium fluoride powder with a potassium content of 1.8 ppm was used as raw material for manufacturing Comparative Example 1 of crystalline calcium fluoride. Quantitative determination of the potassium concentration within the powder raw material was carried out by the atomic absorption spectrochemical analysis.

The powder raw material did not undergo high temperature heat treatment.

The vertical Bridgeman method was used for crystal growth. Two heater elements (with independent power circuits, independent settings, and independent control) were provided above and below the solid-melt interface to control the temperature gradient at the solid-melt interface. At the interface, the temperatures of the heater elements were measured by radiation thermometers (pyrometers). The distance between the measurement locations of these pyrometers was set to 10 cm. For example, the temperature gradient would be determined to be 5° C./cm if the temperature difference of the top and bottom heater elements was 50° C. The powder raw material was charged in a chamber, and the chamber was vacuumed. The temperature was raised under precise temperature control, and the raw material was melted. The temperature gradient was set to 5° C./cm. Then crystallization was carried out by a pulling-down scheme at a rate of 1 mm per hour from the high temperature zone to the low temperature zone.

A permanence test sample was prepared from the crystalline calcium fluoride obtained in this manner. This sample was 5.08 cm (2 inches) in diameter and 2.54 cm (1 inch) in thickness. Accuracy of thickness processing was ±0.01 cm. The two parallel surfaces were parallel within 30 sec. The RMS surface roughness of the mirror-polished surfaces was less than 5 Å. The mirror-polished sample surfaces underwent surface cleaning treatment: ultrasonic cleaning using organic solvent, followed by rinsing with purified water, and then drying using isopropyl alcohol vapor.

The transmissivity of this sample at 140 to 200 nm was measured by spectroscopy (spectroscopic transmissivity). Permanence testing was carried out using a light source producing vacuum ultraviolet light with a 146 nm central wavelength. The irradiation device was a head-on type barrier discharge lamp. The intensity of the vacuum ultraviolet radiation from this lamp was 15 mW/cm$^2$. The entire vacuum ultraviolet light path was purged with nitrogen during the permanence testing to prevent absorption by oxygen. After irradiation of the sample by vacuum ultraviolet light for 1 hour, spectroscopic transmissivity was measured again at 140 to 200 nm. FIG. 2 shows the transmissivity curves (including multiple reflections) for before and after the irradiation with the vacuum ultraviolet light. As shown in FIG. 2, despite excellent transmissivity prior to irradiation by vacuum ultraviolet light, a large decline in transmissivity occurred upon irradiation by vacuum ultraviolet light. The potassium content of the sample was measured by the atomic absorption spectrochemical analysis and found to be 1.6 ppm.

Potassium addition and growth experiments were carried out to confirm that the potassium contamination contributes degradation of transmissivity upon irradiation by vacuum ultraviolet light.

Experiment

To further investigate the potassium contamination contribution to the degradation of transmissivity, a potassium addition and growth experiment was carried out as follows.

A 0.5 ppm potassium-containing calcium fluoride powder was used for manufacturing crystalline calcium fluoride in this experiment. Quantitative determination of the potassium concentration within the powder raw material was carried out by the atomic absorption spectrochemical analysis.

This powder raw material underwent high temperature heat treatment. A container was provided with 10 kg of powder raw material. The container was placed at a prescribed position within a high temperature heat treatment apparatus, and then evacuation of air was started. After vacuumed for over 1 hour, a pressure below 0.001 atm was achieved. Then the container was heated to 1000° C. during a 1 hour time period. After maintaining the container for 3 hours at the high temperature, the temperature was dropped to room temperature during a 10 minute time period. A 5 hour time period was required for the powder raw material to cool down to near room temperature. Vacuum was cut off, and the powder raw material was taken out.

The vertical Bridgeman method was used for crystal growth. The powder raw material that had undergone the high temperature heat treatment above and 4 g of potassium fluoride reagent were charged into a crucible. Vacuum was pulled on the equipment. The temperature was raised under precise temperature control, and the raw material was melted. Although a wide temperature difference between the upper and lower heater elements would have been desirable in order to lower the potassium content, the temperature gradient was reduced to 8° C./cm in order to leave some of the added potassium in the crystal as remnant potassium. Then crystallization was carried out by a pulling-down scheme at a rate of 1 mm per hour from the high temperature zone to the low temperature zone.

A permanence test sample was prepared from the crystalline calcium fluoride obtained in this manner. This sample was 5.08 cm (2 inches) in diameter and 2.54 cm (1 inch) in thickness. Accuracy of thickness processing was ±0.01 cm. The two parallel surfaces were parallel within 30 sec. The RMS surface roughness of the mirror-polished surfaces was less than 5 Å. The mirror-polished sample surfaces underwent surface cleaning treatment: ultrasonic cleaning using organic solvent, followed by rinsing with purified water, and then drying using isopropyl alcohol vapor.

The transmissivity (including reflections) of this sample at 146 nm was measured. Permanence testing was carried out using a light source producing vacuum ultraviolet light with a 146 nm central wavelength. The irradiation device was a head-on type barrier discharge lamp manufactured by Ushio Denki K.K. The intensity of the vacuum ultraviolet radiation from this lamp was 15 mW/cm$^2$. The entire vacuum ultraviolet light path was purged with nitrogen during the permanence testing to prevent absorption by oxygen. After irradiation of the sample by vacuum ultraviolet light for 1 hour, the transmissivity at 146 nm was measured again. A difference arose between the pre-irradiation transmissivity and the post-irradiation transmissivity due to irradiation by vacuum ultraviolet light, and the permanence test result for this sample was found to be 17.8%. Furthermore, the potassium content of the sample was measured by the atomic absorption spectrochemical analysis and found to be 2.8 ppm.

Figure 3:
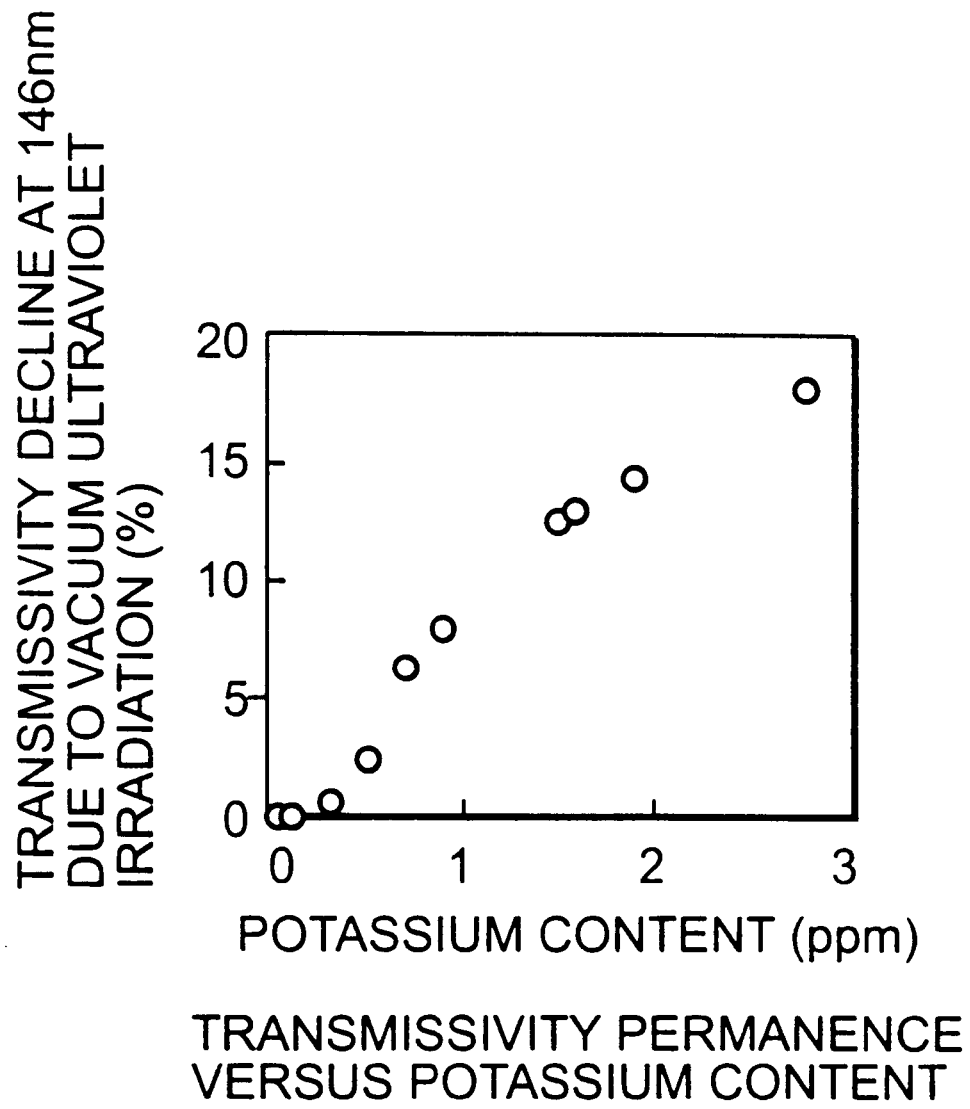
FIG. 3 shows a graph indicating the relationship between potassium content and transmissivity permanence test results upon irradiation by 146 nm wavelength vacuum ultraviolet light.

In order to further examine quantitatively the relationship between potassium content in the crystalline calcium fluoride and the transmissivity decrease, the quantity of potassium fluoride reagent added upon crystallization was varied, and plural samples were produced. These samples underwent the permanence testing and quantitative analysis of potassium content. The results are plotted in FIG. 3. As shown in FIG. 3, a minute quantity of potassium contained within the calcium fluoride crystal causes a decline of transmissivity upon irradiation by vacuum ultraviolet light. In particular, the transmissivity permanence is excellent for calcium fluoride crystals with potassium contents below about 0.5 ppm. Therefore, it was discovered that the use of calcium fluoride crystals with potassium contents below about 0.5 ppm is preferable for lenses of an optical lithography apparatus that utilizes a vacuum ultraviolet light source.

WORKING EXAMPLE 2

Next, a preferred example of crystalline calcium fluoride which is designed especially for use in an optical lithography apparatus that utilizes an $F_2$ laser as a light source is explained.

A 0.3 ppm potassium-containing calcium fluoride powder was used for manufacturing crystalline calcium fluoride of this example. Quantitative determination of the potassium concentration within the powder raw material was carried out by the atomic absorption spectrochemical analysis.

This powder raw material underwent a high temperature heat treatment. The powder raw material of 100 kg was charged into a container. The container was placed at a prescribed position within a high temperature heat treatment apparatus, and then evacuation of air was started. After pulling a vacuum for over 3 hours, a pressure below 0.001 atm was achieved. Then the container was heated to 1200° C. during a 1 hour time period. After maintaining the container for 5 hours at the high temperature, the temperature was dropped to room temperature during a 30 minute time period. A 10 hour time period was required for the powder raw material to cool down to near room temperature. Vacuum was cut off, and the powder raw material was taken out.

The vertical Bridgeman method was used for crystal growth. Two heater elements with independent power circuits were provided above and below and were separately controlled. The temperatures of the heater elements were measured by radiation thermometers (pyrometers). The powder raw material that underwent the heat treatment was charged in a container, and vacuum was pulled on the equipment. The temperature was raised to 1400° C., and the raw material powder was melted. The temperature gradient was set to 15° C./cm since a larger temperature differential between the heater elements is desirable. Then crystallization was carried out by a pulling-down scheme at a rate of 1 mm per hour from the high temperature zone to the low temperature zone.

A test sample was prepared from the crystalline calcium fluoride obtained in this manner. The potassium content of the sample was measured by atomic absorption spectrochemical analysis and found to be 0.09 ppm.

An optical lens was manufactured from this crystalline calcium fluoride. This optical lens was used in an optical lithography apparatus utilizing a 157 nm wavelength vacuum ultraviolet light source ($F_2$ laser), and superior transmissivity and transmissivity permanence sufficient for practical use were confirmed.

WORKING EXAMPLE 3

Next, a preferred example of crystalline calcium fluoride, which is practically suitable for use in an optical lithography apparatus that utilizes an ArF laser as a light source is explained.

A 0.3 ppm potassium-containing calcium fluoride powder was used for manufacturing crystalline calcium fluoride of this example. Quantitative determination of the potassium concentration within the powder raw material was carried out by the atomic absorption spectrochemical analysis.

This powder raw material underwent a high temperature heat treatment. The powder raw material of 100 kg was charged into a container. The container was placed at a prescribed position within a high temperature heat treatment apparatus, and then evacuation of air was started. After pulling of vacuum for over 3 hours, a pressure below 0.001 atm was achieved. Then the container was heated to 1200° C. during a 1 hour time period. After maintaining the container for 5 hours at that high temperature, the temperature was dropped to room temperature during a 30 minute time period. A 10 hour time period was required for the powder raw material to cool down to near room temperature. Vacuum was cut off, and the powder raw material was taken out.

The vertical Bridgeman method was used for crystal growth. Two heater elements with independent power circuits were provided above and below and were separately controlled. Temperature of each heater element was measured by radiation thermometers (pyrometers). The powder raw material was charged in a container, and vacuum was pulled on the equipment. The temperature was raised to 1400° C., and the raw material powder was melted. The temperature gradient was set to 20° C./cm since a larger temperature differential between the heater elements is desirable. Then crystallization was carried out by a pulling-down scheme at a rate of 1 mm per hour from the high temperature zone to the low temperature zone.

A test sample was prepared from the crystalline calcium fluoride obtained in this manner. The potassium content of the sample was measured by the atomic absorption spectrochemical analysis and found to be 0.07 ppm.

An optical lens was manufactured from this crystalline calcium fluoride. This optical lens was used in an optical lithography apparatus utilizing a 193 nm wavelength vacuum ultraviolet light source (ArF excimer laser), and superior transmissivity and transmissivity permanence sufficient for practical use were confirmed.

WORKING EXAMPLE 4

A 0.4 ppm potassium-containing calcium fluoride powder was used for manufacturing crystalline calcium fluoride of this example. Quantitative determination of the potassium concentration within the powder raw material was carried out by the atomic absorption spectrochemical analysis.

This powder raw material underwent a high temperature heat treatment. The powder raw material of 100 kg was charged into a container. The container was placed at a prescribed position within a high temperature heat treatment apparatus, and then evacuation of air was started. After pulling of vacuum for over 3 hours, a pressure below 0.001 atm was achieved. Then the container was heated to 1200° C. during a 1 hour time period. After maintaining the container for 1 hour at that high temperature, the temperature was dropped to room temperature during a 30 minute time period. A 10 hour time period was required for the powder raw material to cool down to near room temperature. Vacuum was cut off, and the powder raw material was taken out.

The vertical Bridgeman method was used for crystal growth. Two heater elements with independent power circuits were provided above and below and were separately controlled. The temperatures of the heater elements were measured by radiation thermometers (pyrometers). The powder raw material that had undergone high temperature heat treatment was charged into a container, and vacuum was pulled on the equipment. Temperature was raised to 1400° C., and the raw material powder was melted. The temperature gradient was set to 10° C./cm since a larger temperature differential between the heater elements is desirable. Then crystallization was carried out by a pulling-down scheme at a rate of 1 mm per hour from the high temperature zone to the low temperature zone.

A test sample was prepared from the crystalline calcium fluoride obtained in this manner. The potassium content of the sample was measured by the atomic absorption spectrochemical analysis and found to be 0.3 ppm.

Moreover, a permanence test sample was prepared from the crystalline calcium fluoride obtained in this manner. This sample was 5.08 cm (2 inches) in diameter and 2.54 cm (1 inch) in thickness. The two parallel surfaces were parallel within 30 sec. The RMS surface roughness of the mirror-polished surfaces was less than 5 Å. The mirror-polished sample surfaces underwent surface cleaning treatment: ultrasonic cleaning using organic solvent, followed by rinsing with purified water, and then drying using isopropyl alcohol vapor.

Permanence testing of this sample was performed using a 157 nm wavelength $F_2$ laser as the irradiation light. The $F_2$ laser utilized a laser resonator manufactured by Lambda Physik (LPF series). Laser intensity was measured using a joulemeter (J25 series, manufactured by Molectron). The light path of the $F_2$ laser was placed entirely in high purity nitrogen atmosphere in order to prevent absorption by oxygen, etc. The $F_2$ laser produced pulsed light with a pulse frequency of 200 Hz. The $F_2$ laser energy density was 10 $mJ/(cm^2 \cdot pulse)$, and the sample was irradiated by 10,000 pulses (50 seconds). The post-irradiation transmissivity decline was found to be 3.6% per 2.54 cm (1 inch) of sample thickness.

An optical lens was manufactured from this crystalline calcium fluoride. This optical lens was used in an optical lithography apparatus utilizing an $F_2$ laser light source, and superior transmissivity and transmissivity permanence sufficient for practical use were achieved.

WORKING EXAMPLE 5

A 0.4 ppm potassium-containing calcium fluoride powder was used for manufacturing crystalline calcium fluoride of this example. Quantitative determination of the potassium concentration within the powder raw material was carried out by the atomic absorption spectrochemical analysis.

This powder raw material underwent a high temperature heat treatment. The powder raw material of 100 kg was charged into a container. The container was placed at a prescribed position within a high temperature heat treatment apparatus, and then evacuation of air was started. After pulling of vacuum for over 3 hours, a pressure below 0.001 atm was achieved. Then the container was heated to 1200° C. during a 1 hour time period. After maintaining the container for 1 hour at that high temperature, the temperature was dropped to room temperature during a 30 minute time period. A 10 hour time period was required for the powder raw material to cool down to near room temperature. Vacuum was cut off, and the powder raw material was taken out.

The vertical Bridgeman method was used for crystal growth. Two heater elements with independent power circuits were provided above and below and were separately controlled. The temperatures of the heater elements were measured by radiation thermometers (pyrometers). The powder raw material that had undergone high temperature heat treatment was charged into a container, and vacuum was pulled on the equipment. Temperature was raised to 1400° C., and the raw material powder was melted. The temperature gradient was set to 10° C./cm since a larger temperature differential between the heater elements is desirable. Then crystallization was carried out by a pulling-down scheme at a rate of 1 mm per hour from the high temperature zone to the low temperature zone.

Subsequently, a heat treatment was performed on the calcium fluoride crystal obtained above. The calcium fluoride crystal was heated to 1000° C. and maintained at that temperature for a predetermined period. The heated crystal was then gradually cooled at a rate of 5° C./hr. During this heat treatment, the interior of the heat temperature apparatus, in particular, a stand holding the crystal, was kept clean in order to avoid contamination of potassium into the calcium fluoride crystal.

The content of potassium in the resulting calcium fluoride crystal was quantitatively determined and found to be comparable to the value in Working Example 4. Also, transmissivity permanence was tested and found to have excellent results comparable to Working Example 5.

It will be apparent to those skilled in the art that various modifications and variations can be made in the manufacturing method, evaluation method, and optical lithography apparatus for a light-transmitting optical component of the present invention without departing from the spirit or scope of the invention. Thus, it is intended that the present invention covers the modifications and variations of this invention provided they come within the scope of the appended claims and their equivalents.

What is claimed is:

1. An optical lithography apparatus comprising:

an illumination optical system that emits exposure light of a wavelength less than about 200 nm towards a mask having a pattern; and a projection optical system that projects an image of the pattern on the mask onto a substrate via the exposure light, wherein at least one of the illumination optical system and the projection optical system includes a light-transmitting optical member formed of crystalline calcium fluoride with a potassium content of less than about 0.5 ppm.

* * * * *